United States Patent
Song et al.

(10) Patent No.: US 10,271,126 B2
(45) Date of Patent: *Apr. 23, 2019

(54) EARPHONE NOISE REDUCTION METHOD AND APPARATUS

(71) Applicant: SHENZHEN GRANDSUN ELECTRONIC CO., LTD., Shenzhen, Guangdong (CN)

(72) Inventors: Yanan Song, Shenzhen (CN); Haiquan Wu, Shenzhen (CN); Ruiwen Shi, Shenzhen (CN); Xinian Geng, Shenzhen (CN); Gouzhong Du, Shenzhen (CN); Jiayun Xu, Shenzhen (CN)

(73) Assignee: SHENZHEN GRANDSUN ELECTRONIC CO., LTD., Shenzhen, Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/544,815

(22) PCT Filed: Jan. 26, 2015

(86) PCT No.: PCT/CN2015/071567
§ 371 (c)(1),
(2) Date: Jul. 19, 2017

(87) PCT Pub. No.: WO2016/119106
PCT Pub. Date: Aug. 4, 2016

(65) Prior Publication Data
US 2018/0020282 A1    Jan. 18, 2018

(51) Int. Cl.
*H04R 1/10* (2006.01)
*G10K 11/178* (2006.01)
*A61F 11/14* (2006.01)

(52) U.S. Cl.
CPC ............ *H04R 1/1083* (2013.01); *A61F 11/14* (2013.01); *G10K 11/178* (2013.01); *H04R 1/10* (2013.01);
(Continued)

(58) Field of Classification Search
None
See application file for complete search history.

(56) References Cited

U.S. PATENT DOCUMENTS

2010/0172510 A1*  7/2010  Juvonen .............. G10K 11/178
                                               381/71.6
2011/0317848 A1* 12/2011  Ivanov ................. H04R 3/005
                                               381/94.2
(Continued)

FOREIGN PATENT DOCUMENTS

CN    101951422 A    1/2011
CN    103024631 A    4/2013
(Continued)

OTHER PUBLICATIONS

Yi et al, "Noise reduction method, device and mobile terminal." Google patent translation of CN103716438. pp. 1-6. Apr. 9, 2014.*
(Continued)

*Primary Examiner* — Curtis A Kuntz
*Assistant Examiner* — Qin Zhu
(74) *Attorney, Agent, or Firm* — Conley Rose, P.C.; Grant Rodolph

(57) ABSTRACT

An earphone noise reduction method and apparatus, which are applicable to the technical field of wearable devices. The earphone noise reduction method can include collecting, using an earphone microphone, a noise signal of an environment where the earphone microphone is placed. The method can also include transmitting the noise signal to a connected terminal or transmitting a noise value correspond-
(Continued)

ing to the noise signal to the connected terminal. The method can further include receiving a judgement result returned by the terminal, and enabling a noise reduction function or disabling the noise reduction function according to the judgement result. Embodiments of the present disclosure can be realized without keys or toggle switches for noise reduction adjustment on earphones. Embodiments of the present disclosure are capable of automatic noise reduction, thereby improving the integration degree of the earphones and also enhancing the battery life of the earphones.

14 Claims, 4 Drawing Sheets

(52) U.S. Cl.
CPC ...... *H04R 1/1041* (2013.01); *A61F 2011/145* (2013.01); *G10K 2210/1081* (2013.01); *G10K 2210/3011* (2013.01); *G10K 2210/3012* (2013.01); *G10K 2210/3016* (2013.01); *G10K 2210/3051* (2013.01)

(56) References Cited

U.S. PATENT DOCUMENTS

| | | | | |
|---|---|---|---|---|
| 2012/0076312 | A1* | 3/2012 | Iyengar | G10L 21/0208 381/57 |
| 2012/0078397 | A1* | 3/2012 | Lee | G10L 25/78 700/94 |
| 2012/0128164 | A1* | 5/2012 | Blamey | H04R 5/04 381/28 |
| 2013/0022213 | A1* | 1/2013 | Alcock | G10K 11/1782 381/71.6 |
| 2013/0051589 | A1* | 2/2013 | Ide | H04R 1/1025 381/309 |
| 2014/0126733 | A1* | 5/2014 | Gauger, Jr. | G10K 11/178 381/71.6 |
| 2015/0243272 | A1* | 8/2015 | Ozluturk | G10K 11/175 381/71.6 |
| 2016/0286297 | A1* | 9/2016 | Wang | H04R 1/1016 |
| 2017/0230747 | A1* | 8/2017 | Song | H04R 1/1083 |

FOREIGN PATENT DOCUMENTS

| | | |
|---|---|---|
| CN | 103078997 A | 5/2013 |
| CN | 103716438 A | 4/2014 |

OTHER PUBLICATIONS

PCT International Search Report; Application No. PCT/CN2015/071567; dated Apr. 29, 2015; 5 pages.
PCT Written Opinion of the International Searching Authority; Application No. PCT/CN2015/071567; dated Apr. 29, 2015; 3 pages. (No English translation available.).

* cited by examiner

EARPHONE NOISE REDUCTION METHOD AND APPARATUS

CROSS-REFERENCE TO RELATED APPLICATIONS

This application is a U.S. National Stage of International Patent Application No. PCT/CN2015/071567 filed on Jan. 26, 2015, by Yanan Song, et al. entitled, "Earphone Noise Reduction Control Method and Apparatus", which is incorporated by reference herein as if reproduced in its entirety.

TECHNICAL FIELD

The present disclosure relates to the technical field of wearable devices, and in particular to an earphone noise reduction method and apparatus.

BACKGROUND

As one of the four major internationally-recognized pollutions, noise pollution has become increasingly serious with urban development and technological progress. When a user plays audio through a terminal external earphone, he/she can utilize an earphone noise reduction method to reduce environmental noise and protect his/her hearing.

Earphone noise reduction methods in the prior art are achieved in two ways. The first way is blocking the noise physically using the earphones, such that the noise cannot reach the user's ears; the second way is configuring the earphones to collect the noise, then reverse and superpose the noise inside the earphones so as to compensate the noise inside the earphones, such that the noise cannot be perceived by the ears.

However, the existing earphone noise reduction methods require keys or toggle switches arranged on the earphones configured to regulate the noise reduction, which is unfavorable for advanced integration of the earphones, and automatic noise reduction functions cannot be enabled or disabled in time. The reason is that the existing earphone noise reduction methods, as found in the first way and the second way, all utilize the keys or toggle switches on the earphones to enable or disable the noise reduction function manually. This generally results in inappropriate use of the noise reduction function because of the user's subjective misplay or distraction. For example, when the noise is high enough to damage the user's hearing, but the noise reduction function is not enabled in time, the noise may damage the user's hearing; or when environmental noise cannot be perceived any more, but the noise reduction function is still enabled. Therefore, the noise reduction function cannot be enabled or disabled in time, which incurs unnecessary power consumption and, in the case of battery-powered earphones, decreases the battery life of the earphones. Meanwhile, the earphone noise reduction methods in the prior art require the manufacturer to arrange hardware configured for regulating noise reduction on the earphones, which decreases the integration degree of the earphones.

SUMMARY

The present disclosure provides an earphone noise reduction method, which improves upon prior earphone noise reduction methods, such as the use of keys or toggle switches for regulating noise reduction are arranged on the earphones, which is unfavorable for advanced integration of the earphones, and the noise reduction function that cannot be enabled or disabled in time.

The embodiments of the present application can include earphone noise reduction methods that include utilizing an earphone microphone to collect noise signal of an environment where the earphone microphone is positioned. The method can also include transmitting the noise signal to a connected terminal, or transmitting a noise value corresponding to the noise signal to the connected terminal. The method can further include receiving a judgement result returned by the terminal, and enabling a noise reduction function or disabling the noise reduction function according to the judgement result.

Embodiments of the present disclosure can also include an earphone noise reduction apparatus that includes a noise signal collection module configured to utilize an earphone microphone to collect noise signal of an environment where the earphone microphone is positioned. The apparatus can also include a noise signal transmitting module configured to transmit the noise signal to a connected terminal, or transmit a noise value corresponding to the noise signal to the connected terminal. The apparatus can further include a noise reduction function module configured to receive a judgement result returned by the terminal, and enable a noise reduction function or disable the noise reduction function according to the judgement result.

In the embodiments of the present disclosure, the judgement result returned by the terminal can be received, and the noise reduction function can be enabled or disabled according to the judgement result, which improves upon earphone noise reduction methods. Embodiments of the present disclosure can include benefits, such as the elimination of the use of a hardware switch for noise reduction adjustment on earphones, and automatic noise reduction that does not include the use of a hardware switch on the earphones because noise reduction can be automatically enabled or disabled, thereby improving the integration degree of the earphones, decreasing unnecessary power consumption and enhancing the battery life of the earphones.

DETAILED DESCRIPTION OF THE PREFERRED EMBODIMENT

In order to further clarify the purposes, technical solutions and advantages of the present disclosure, embodiments of the present disclosure will be described in further detail with reference to the accompanying drawings. It is to be understood that the specific embodiments described herein are merely illustrative of the application and are not intended to limit the application.

Embodiment 1

Figure 1:
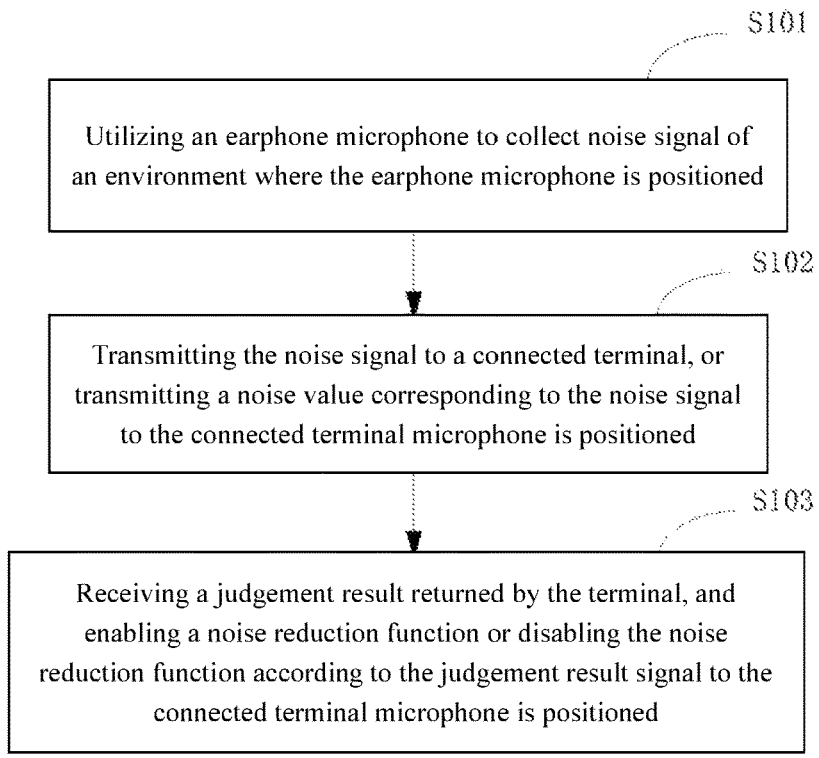
FIG. 1 is an implementation flow chart of an earphone noise reduction method provided by an embodiment of the present application.

FIG. 1 is an implementation flow chart of and embodiment configured for earphone noise reduction.

At block S101, earphone microphone is utilized to collect a noise signal of an environment where the earphone microphone is positioned.

Embodiments for implementing the utilizing of an earphone microphone to collect noise signal of an environment where the earphone microphone is positioned are described in detail below.

The first implementation includes an earphone microphone that is utilized to collect noise signal of an environment where the earphone microphone is positioned every predetermined detection interval.

It should be understood that since a noise signal of the environment does not change significantly within a period of time, power consumption of the earphones can be further saved by detecting the noise signal of the environment once every predetermined detection interval.

The second implementation includes utilizing an earphone microphone to collect a noise signal of the environment where the earphone microphone is positioned while a distance between the geographic position where the earphones are currently positioned and a geographic position where the noise signal of the environment was collected last time is not less than a predetermined distance.

It should be understood that if the distance between the geographic position where the earphones are currently positioned, and the geographic position where the noise signal of the environment was collected last time, exceeds the predetermined distance, the environment may change accordingly because of geographical distance. A further detection of the noise signal of the environment is performed in order to inform the user of the changing situation of the signal noise intensity of the environment where the user is currently positioned.

It should be understood that a situation can arise where the distance that the earphones move does not exceed the predetermined distance, but the moving duration is relatively long. Therefore, in order to compensate for significant changes in noise signal intensity where the earphones are positioned during the long moving duration, block S101 can further include that when a distance between the geographic position where the earphones are currently positioned and the geographic position where the noise signal of the environment, where the earphone microphone was positioned, was collected last time does not exceed the predetermined distance, but the time duration since the noise signal of the environment was detected last time by the earphones exceeds a predetermined detection interval, then the earphones also collect noise signal where the earphone microphone is positioned.

Therefore, accuracy and intensity of the noise signal detection of the environment where the earphone microphone is positioned is further improved.

Also, the earphones' native Global Positioning System (GPS) function can be utilized to detect the distance from the current position of the earphones to the graphical position where the noise signal of the environment, where the earphones were positioned, was detected last time, so as to determine whether the detected distance exceeds a predetermined distance.

At block S102, a noise signal is transmitted to a connected terminal, or a noise value corresponding to the noise signal is transmitted to the connected terminal.

The noise signal can be transmitted directly to the connected terminal, or alternatively, the noise signal can be sampled to generate a noise value corresponding to the noise signal, which is then transmitted to a terminal. The terminal can be a device that exchanges instructions and data with the earphones in a wired or wireless mode.

The terminal can include, but is not limited to, smart phones, tablets, laptops, desktop computers and smart televisions.

The terminal can be connected with the earphones through any wired modes or any wireless modes. The wireless modes include but are not limited to Bluetooth, Wireless Fidelity (WIFI), third generation (3G), fourth generation (4G) and fifth generation (5G). The earphones can lack a display screen but can be capable of enabling or disabling noise reduction functionally such that the earphones do not provide users with any visualized information and suggestions; the earphones may also lack a flexible scheme for regulating the noise reduction, but instead transmit the noise signal or the noise value corresponding to the noise signal to the connected terminal such that the earphones need not to judge the noise signal, thereby decreasing the burden of a processor of the earphones for processing data. Meanwhile, the earphones can be capable of receiving schemes for regulating the noise reduction transmitted by the connected terminal.

At block S103, the embodiment includes receiving a judgement result returned by the terminal, and enabling a noise reduction function or disabling the noise reduction function according to the judgement result.

The earphones receive the judgement result returned by the terminal through a default communication interface, and based on the judgement result, detect whether the current state of the noise reduction function is identical with the judgement result. If identical, then the current state of the noise reduction function is maintained, otherwise, the current state of the noise reduction function is changed and the noise reduction function is enabled or disabled.

In some embodiments of the present disclosure, the judgement result returned by the terminal is received, and the noise reduction function is enabled or disabled according to the judgement result, which solves the problems in the existing earphone noise reduction methods that the requirement for arranging keys or toggle switches for noise reduction adjustment on earphones is unfavorable for advanced integration of the earphones and the noise reduction function cannot be enabled or disabled in time. By replacing traditional manual noise reduction with automatic noise reduction, the earphones are not only more humanized and intelligent, but also capable of meeting the requirement of the user for hearing health.

Embodiment 2

Figure 2:
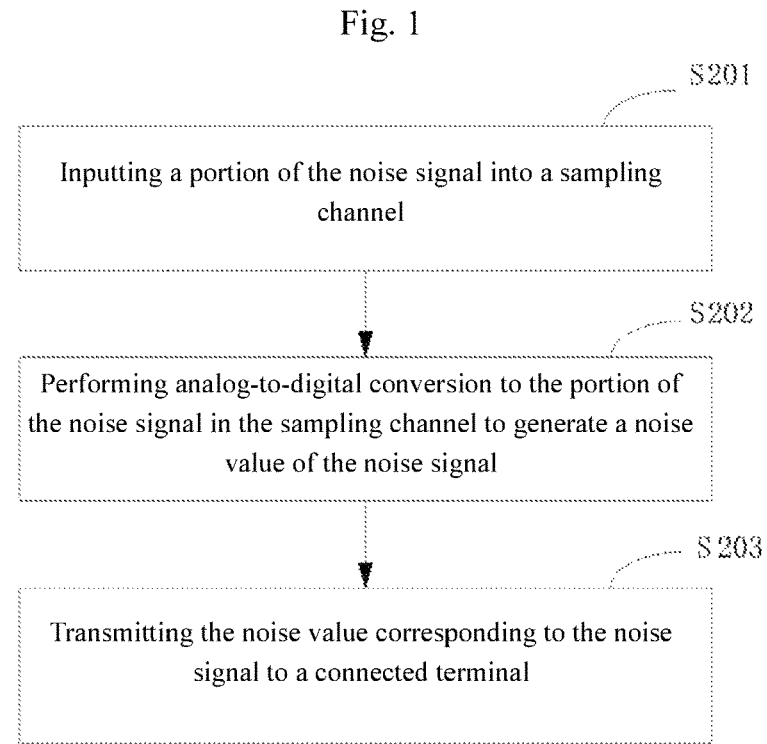
FIG. 2 is an implementation flow diagram of S102 of the earphone noise reduction method provided by an embodiment of the present application.

FIG. 2 is an implementation flow diagram of S102 of the earphone noise reduction method provided by an embodiment of the present disclosure, which is described in detail below.

At block S201, a portion of the noise signal is input into a sampling channel.

At block S202, an analog-to-digital conversion is performed on the portion of the noise signal in the sampling channel to generate a noise value of the noise signal.

At block S203, the noise value corresponding to the noise signal is transmitted to a connected terminal.

In some embodiments of the present disclosure, the noise value corresponding to the noise signal is transmitted to the connected terminal, which is convenient for receiving a judgement result generated by the terminal based on the noise signal, and enabling a noise reduction function or disabling the noise reduction function according to the judgement result.

Embodiment 3

Figure 3:
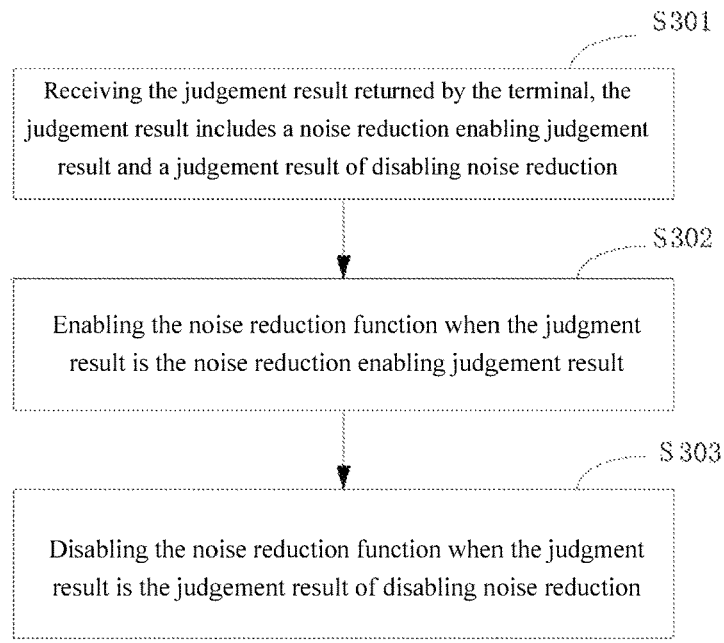
FIG. 3 is an implementation flow diagram of S103 of the earphone noise reduction method provided by an embodiment of the present application.

FIG. 3 is an implementation flow diagram of S103 of the earphone noise reduction method provided by an embodiment of the present disclosure, which is described in detail as follows.

At block S301, the judgement result is received from the terminal. The judgement result can include a judgement result of enabling noise reduction and a judgement result of disabling noise reduction.

At block S302, the noise reduction function is enabled when the judgment result is representative of a result for enabling noise reduction.

When the judgment result is representative of a result for enabling noise reduction, whether the current state of the noise reduction function of the earphones is enabled is detected; when the current state of the noise reduction function of the earphones is not in enabled state, then the noise reduction function is adjusted to be enabled.

At block S303, the noise reduction function is disabled when the judgment result is representative of a result for disabling noise reduction.

When the judgment result is representative of result for disabling noise reduction, whether the current state of the noise reduction function of the earphones is disabled is detected; when the current state of the noise reduction function of the earphones is not in disabled state, then the noise reduction function is adjusted to be disabled.

In some embodiments of the present disclosure, the noise reduction function is enabled or disabled according to the judgement result, which achieves automatic noise reduction function of the earphones, improves the integration degree of the earphones, and enhances the battery life of the earphones.

Embodiment 4

This embodiment of the present disclosure describes a preferred implementation process of the application in a practical application, which is described in detail below.

The apparatus can include two processing modes after the earphone microphone collects noise signal of the environment where the earphone microphone is positioned.

If an analogue noise reduction technology is used, then environment noise signal is divided into two paths: one path utilizes analog to digital conversion (ADC) to perform numerical calculations so as to obtain a decibel value of the noise signal; the other path acts as an analog signal to be input into an active noise reduction module.

If a digital noise reduction technology is used, then the environmental noise signal is directly input into the active noise reduction module and a calculation is performed inside the module and the decibel value of the noise signal is returned.

The decibel value is generally transmitted to the terminal via any transmission mode. For example, the transmission modes include but are not limited to Bluetooth transmission mode, WIFI transmission mode, 3G transmission mode, 4G transmission mode, and 5G transmission mode.

After receiving the decibel value of the noise signal, the terminal analyzes the decibel value and returns two contents:

The first content: displaying an analysis result of current environmental noise signal on the terminal, and providing suggestions for a user about how to use the earphones.

The second content: sending corresponding instruction automatically to the earphone, and adjusting the function of the earphones to a usage state which is favorable for the current noise environment.

If the user refuses the best usage state of the earphones controlled by the terminal, the user may regulate the usage state of the earphones by adjusting the terminal or the earphones.

Embodiment 5

This embodiment of the present disclosure describes preferred implementation processes for three different scenarios, which are described below.

In the first scenario, a smartphone provides a noise reduction suggestion based on the decibel value of environmental noise signal collected by the earphones, which is described in detail as follows.

After the earphone microphone collects the environmental noise signal, the environmental noise signal is divided into two paths. One path utilizes ADC conversion to perform numerical calculation so as to obtain a decibel value of the noise signal, which is 80 dB.

The obtained decibel value is transmitted to the smartphone, for example wirelessly, such as via Bluetooth.

After receiving the decibel value, the smartphone analyzes the decibel value, and learns that noise with a decibel value, for example of 80 dB, would significantly damage a human's hearing, and the volume has been overly increased by the current user.

After the noise reduction function is enabled, current volume level used by the user would be overly high; therefore, the smartphone would display an analysis result and application suggestion. The analysis result and application suggestion are as follows:

The smartphone suggests that the user should enable the earphone noise reduction function, and turn down the volume level of the earphones or phone so as to protect the user's hearing.

Alternatively, the smartphone can transmit instructions for enabling the active noise reduction function to the earphones automatically, and turn down the volume level of the earphones.

In the second scenario, a tablet provides a noise reduction suggestion based on the decibel value of environmental noise signal collected by the earphones, which is described below.

After the earphone microphone collects the environmental noise signal, the environmental noise signal is divided into two paths: one path utilizes ADC conversion to perform numerical calculation so as to obtain a decibel value of the noise signal, for example 20 dB.

The obtained decibel value is transmitted to the table, for example wirelessly, such as via WIFI.

After receiving the decibel value, the tablet analyzes the decibel value, and learns that noise with a decibel value of 20 dB would not damage a human's hearing significantly, and sound with a decibel value of 20 dB cannot be heard by a human, however, the current user has enabled the noise reduction function. Therefore, the tablet would display an analysis result and application suggestion. For example, the smartphone suggests the user disables the earphone active noise reduction function, or turn up the volume level of the earphones or phone so as to ensure that after the active noise reduction function is disabled, the noise to signal ratio of the sound heard by a human remains unchanged.

Alternatively, the tablet transmits instructions of disabling the active noise reduction function automatically, and turns up the volume level of the earphones.

In the third scenario, a laptop provides noise reduction suggestion based on the decibel value of environmental noise signal collected by the earphones, which is described in detail below.

After the earphone microphone collects the environmental noise signal, the environmental noise signal is input into an active noise reduction module; after being processed by the module, the output decibel value of the noise signal of the current environment is 60 dB.

The obtained decibel value is transmitted to the laptop, for example via a Universal Serial Bus (USB) connection.

After receiving the decibel value, the laptop analyzes the decibel value, and learns that noise with a decibel value of 60 dB would significantly damage a human's hearing, and the noise reduction function has been enabled by the current user. Therefore, the laptop would display an analysis result and application suggestion. Specifically, the laptop suggests the user maintains the current usage state.

The laptop would not send any instruction to the earphones.

Embodiment 6

Figure 4:
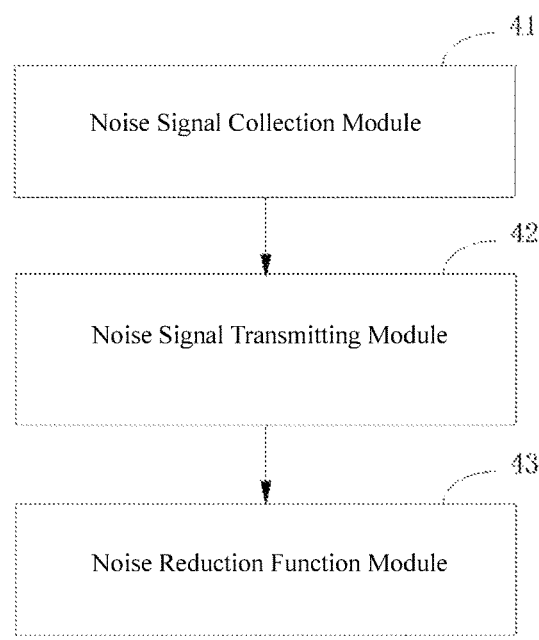
FIG. 4 is a first structural block diagram of an earphone noise reduction apparatus according to an embodiment of the present application.

FIG. 4 is a first structural block diagram of an earphone noise reduction apparatus according to an embodiment of the present disclosure, in which the earphone noise reduction apparatus can run in earphones. For illustration purposes, only portions relevant to the embodiment are shown.

Referring to FIG. 4, the earphone noise reduction apparatus includes a noise signal collection module 41 configured to utilize an earphone microphone to collect noise signal of an environment where the earphone microphone is positioned. The earphone noise reduction apparatus also includes a noise signal transmitting module 42 configured to transmit the noise signal to a connected terminal, or transmit a noise value corresponding to the noise signal to the connected terminal. The earphone noise reduction apparatus further includes a noise reduction function module 43 configured to receive a judgement result returned by the terminal, and enable a noise reduction function or disable the noise reduction function according to the judgement result.

In one implementation of the embodiment, the noise signal collection module 41 of the earphone noise reduction apparatus can be configured to utilize the earphone microphone to collect noise signal of an environment where the earphone microphone is positioned every predetermined detection interval.

In one implementation of the embodiment, the noise signal collection module 41 of the earphone noise reduction apparatus can be configured to utilize the earphone microphone to collect noise signal of an environment where the earphone microphone is positioned when a distance between the geographic position where the earphones are currently positioned and a geographic position where the noise signal of the environment was collected last time is not less than a predetermined distance.

Figure 5:
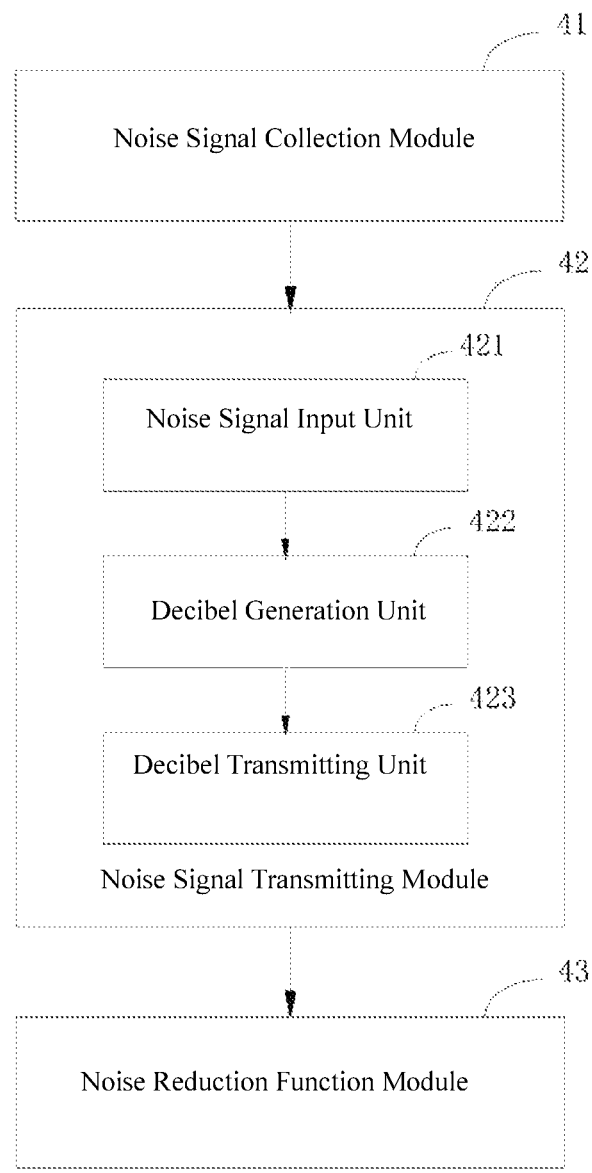
FIG. 5 is a second structural block diagram of the earphone noise reduction apparatus according to an embodiment of the present application.

FIG. 5 is a second structural block diagram of the earphone noise reduction apparatus according to an embodiment of the present disclosure. The noise signal transmitting module 42 of the earphone noise reduction apparatus can include a noise signal input unit 421 configured to input a portion of the noise signal into a sampling channel. The noise signal transmitting module 42 of the earphone noise reduction apparatus can also include a decibel generation unit 422 configured to perform analog-to-digital conversion to the portion of the noise signal in the sampling channel to generate a noise value of the noise signal. The noise signal transmitting module 42 of the earphone noise reduction apparatus can further include a decibel transmitting unit 423 configured to transmit the noise value corresponding to the noise signal to a connected terminal.

Figure 6:
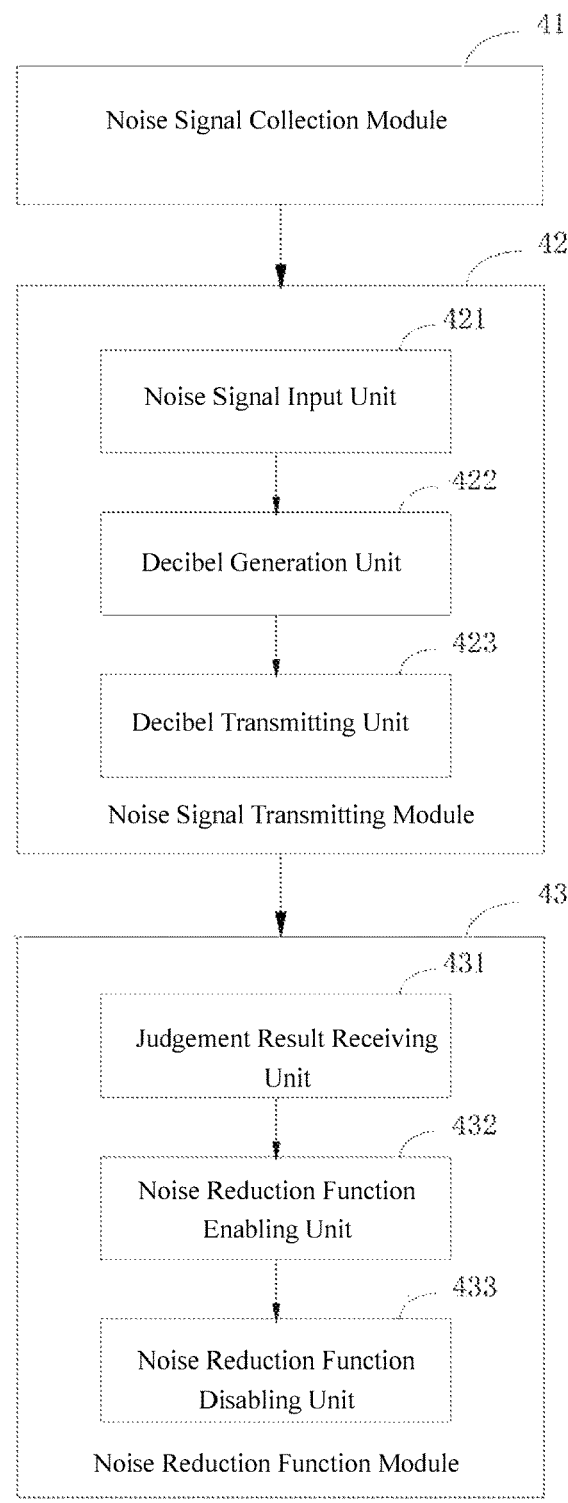
FIG. 6 is a third structural block diagram of the earphone noise reduction apparatus according to an embodiment of the present application.

FIG. 6 is a third structural block diagram of the earphone noise reduction apparatus according to an embodiment of the present application. The noise reduction function module 43 of the earphone noise reduction apparatus includes a judgement result receiving unit 431 configured to receive the judgement result returned by the terminal, the judgement result includes a judgement result of enabling noise reduction and a judgement result of disabling noise reduction. The noise reduction function module 43 of the earphone noise reduction apparatus also includes a noise reduction function enabling unit 432 configured to enable the noise reduction function when the judgment result is the judgement result of enabling noise reduction. The noise reduction function module 43 of the earphone noise reduction apparatus further includes a noise reduction function disabling unit 433 configured to disable the noise reduction function when the judgment result is the judgement result of disabling noise reduction.

The apparatus provided by the embodiments of the present application can be applied to the corresponding process embodiments described above, which can be referred to in the description on the above embodiments and will not be further described.

It will be clear for those skilled in the art that the present disclosure can be realized by means of software and necessary general purpose hardware on the basis of the description of the above embodiments. Mentioned program may be stored in a readable storage medium such as random access memory, flash memory, read only memory, programmable read only memory, electrically erasable programmable memory, registers, and the like. The storage medium is located in a memory, and the processor reads the information in the memory, and executes the methods described in the various embodiments of the present application in conjunction with its hardware.

The contents described above are only specific embodiments of the present disclosure; however, the scope of the present disclosure is not limited thereto. Those skilled in the art will readily envisage any variations or substitutions within the technical scope of the present disclosure, which should be deemed as falling within the scope of the present disclosure. Accordingly, the protection scope of the present disclosure should be based on the protection scope of the claims.

What is claimed is:

1. An earphone noise reduction method comprising:
utilizing a microphone on an earphone to collect a noise signal of an environment where the microphone is positioned when either: a distance between a geographic position where the earphone is currently positioned and a geographic position where the noise signal of the environment where the microphone was positioned when collecting the noise signal of the environment is not less than a predetermined distance; or a distance between the geographic position where the earphone is currently positioned and the geographic position where the noise signal of the environment where the microphone was positioned when collecting the noise signal of the environment was last collected is less than the predetermined distance and a time duration since the noise signal of the environment was last detected by the earphone exceeds a predetermined detection interval, thereby reducing power consumption by a terminal coupled to the earphone as compared to the terminal continuously using the microphone to collect the noise signal of the environment where the microphone is positioned;

transmitting the noise signal or a noise value corresponding to the noise signal to the terminal;

receiving a judgement result from the terminal; and enabling a noise reduction or disabling the noise reduction according to the judgement result.

2. The earphone noise reduction method of claim 1, wherein transmitting the noise value corresponding to the noise signal to the terminal comprises:

inputting a portion of the noise signal into a sampling channel;

performing analog-to-digital conversion (ADC) on the portion of the noise signal in the sampling channel to generate the noise value of the noise signal; and transmitting the noise value corresponding to the noise signal to the terminal.

3. The earphone noise reduction method of claim 1, wherein receiving the judgement result from the terminal and enabling the noise reduction or disabling the noise reduction according to the judgement result comprises: receiving the judgement result from the terminal, wherein the judgement result includes the judgement result of enabling the noise reduction or the judgement result of disabling the noise reduction; enabling the noise reduction when the judgement result is enabling the noise reduction; and disabling the noise reduction when the judgement result is disabling the noise reduction.

4. An earphone comprising:

a microphone; and a processor coupled to the microphone, wherein the processor is configured to:

utilize the microphone to collect a noise signal of an environment where the microphone is positioned when either: a distance between a geographic position where the earphone is currently positioned and a geographic position where the noise signal of the environment where the microphone was positioned when collecting the noise signal of the environment is not less than a predetermined distance; or a distance between the geographic position where the earphone is currently positioned and the geographic position where the noise signal of the environment where the microphone was positioned when collecting the noise signal of the environment was last collected is less than the predetermined distance and a time duration since the noise signal of the environment was last detected by the earphone exceeds a predetermined detection interval, thereby reducing power consumption by a terminal coupled to the earphone as compared to the terminal continuously using the microphone to collect the noise signal of the environment where the microphone is positioned;

transmit the noise signal or a noise value corresponding to the noise signal to the terminal;

receive a judgement result from the terminal; and enable a noise reduction or disable the noise reduction according to the judgement result.

5. The earphone of claim 4, wherein the processor being configured to transact the noise signal or the noise value corresponding to the noise signal to the terminal comprises the processor being configured to:

input a portion of the noise signal into a sampling channel;

perform analog-to-digital conversion (ADC) on the portion of the noise signal in the sampling channel to generate the noise value of the noise signal; and transmit the noise value corresponding to the noise signal to the terminal.

6. The earphone of claim 4, wherein the processor being configured to receive the judgement result from the terminal comprises the processor being configured to: receive the judgement result from the terminal, wherein the judgement result includes the judgement result of enabling the noise reduction or the judgement result of disabling the noise reduction; enable the noise reduction when the judgement result is the judgement result of enabling the noise reduction; and disable the noise reduction when the judgement result is the judgement result of disabling the noise reduction.

7. The earphone of claim 4, wherein after the microphone collects the noise signal of the environment where the microphone is positioned, the noise signal is divided into a first path and a second path, wherein the first path utilizes analog-to-digital conversion (ADC) to perform numerical calculation to obtain a decibel value of the noise signal, and wherein the second path provides an analog signal for the noise reduction.

8. The earphone of claim 4, wherein after the microphone collects the noise signal of the environment where the microphone is positioned, the noise signal is directly input into the processor, and wherein a calculation is performed inside the processor and a decibel value of the noise signal is returned.

9. A system comprising:

a terminal; and an earphone in communication with the terminal, wherein the earphone comprises a microphone and a processor coupled to the microphone, wherein the processor is configured to:

utilize the microphone to collect a noise signal of an environment where the microphone is positioned when either: a distance between a geographic position where the earphone is currently positioned and a geographic position where the noise signal of the environment where the microphone was positioned when collecting the noise signal of the environment is not less than a predetermined distance; or a distance between the geographic position where the earphone is currently positioned and the geographic position where the noise signal of the environment where the microphone was positioned when collecting the noise signal of the environment was last collected is less than the predetermined distance and a time duration since the noise signal of the environment was last detected by the earphone exceeds a predetermined detection interval, thereby reducing power consumption by the terminal as compared to the terminal continuously using the microphone to collect the noise signal of the environment where the microphone is positioned;

transmit the noise signal or a noise value corresponding to the noise signal to the terminal;

receive a judgement result from the terminal; and enable a noise reduction or disable the noise reduction according to the judgement result.

10. The system of claim 9, wherein after the microphone collects the noise signal of the environment where the microphone is positioned, the noise signal is divided into a first path and a second path, wherein the first path utilizes analog-to-digital conversion (ADC) to perform numerical calculation to obtain a decibel value of the noise signal, and wherein the second path provides an analog signal for the noise reduction in the processor.

11. The system of claim 10, wherein the earphone is configured to transmit the decibel value to the terminal, wherein the terminal is configured to: analyze the decibel value; display an analysis result of a current environmental noise signal; and provide a suggestion for a user about how to use the earphone.

12. The system of claim 10, wherein the earphone is configured to transmit the decibel value to the terminal, wherein the terminal is configured to: analyze the decibel value; send corresponding instructions automatically to the earphone; and adjust a function of the earphone to a usage state that favors a current noise environment.

13. The system of claim 12, wherein a final usage state of the earphone is manually regulated by adjusting the terminal even when there is a best usage state of the earphone controlled by the terminal.

14. The system of claim 12, wherein a final usage state of the earphone is manually regulated by adjusting the earphone even when there is a best usage state of the earphone controlled by the terminal.

* * * * *